(12) United States Patent
Auciello et al.

(10) Patent No.: US 7,791,201 B2
(45) Date of Patent: Sep. 7, 2010

(54) INTEGRATION OF DISSIMILAR MATERIALS FOR ADVANCED MULTIFUNCTIONAL DEVICES

(75) Inventors: Orlando Auciello, Bolingbrook, IL (US); John Carlisle, Plainfield, IL (US); Jennifer Gerbi, Champaign, IL (US); James Birrell, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 573 days.

(21) Appl. No.: 11/607,581

(22) Filed: Nov. 30, 2006
(Under 37 CFR 1.47)

(65) Prior Publication Data
US 2008/0246368 A1    Oct. 9, 2008

(51) Int. Cl.
 *H01L 23/48*    (2006.01)
(52) U.S. Cl. ............... 257/759; 257/40; 257/642; 257/E27.117
(58) Field of Classification Search ............ 257/E21.27, 257/759, E27.117
See application file for complete search history.

(56) References Cited

U.S. PATENT DOCUMENTS

| | | | |
|---|---|---|---|
| 6,592,839 B2 * | 7/2003 | Gruen et al. | 423/446 |
| 7,128,889 B2 | 10/2006 | Carlisle | |
| 7,355,235 B2 * | 4/2008 | Wang et al. | 257/310 |
| 7,602,105 B2 * | 10/2009 | Auciello | 310/324 |
| 2003/0032303 A1 * | 2/2003 | Yu et al. | 438/770 |
| 2004/0129202 A1 * | 7/2004 | Gruen et al. | 117/68 |
| 2006/0060864 A1 * | 3/2006 | Gerbi | 257/77 |
| 2006/0199740 A1 | 9/2006 | Auciello | |
| 2007/0040195 A1 | 2/2007 | Auciello | |
| 2007/0220959 A1 | 9/2007 | Sumant | |

OTHER PUBLICATIONS

Fan, W et al. Materials science and integration bases for fabrication of (BaxSr1-x)TiO3 thin film capacitors with layered Cu-based electrode. Nov. 1, 2003. J. Appl. Phys. 94, 6192 (2003).*
Dhote, A.M. et al. Studies of think film growth and oxidation processes for conductive Ti-Al diffusion barrier layers via in situ surface sensitive analytical techniques. Aug. 6, 2001. Appl. Phys. Lett. 79, 800 (2001).*

* cited by examiner

*Primary Examiner*—Thao X Le
*Assistant Examiner*—Ajay K Arora
(74) *Attorney, Agent, or Firm*—Olson & Cepuritis, Ltd.

(57) ABSTRACT

A device including a layered heterostructure with an oxygen-containing material, with a carbon layer and an amorphous oxygen diffusion barrier protecting the carbon layer from etching by oxygen. One or more of a metal, a carbide or an oxide may be in contact with the amorphous oxygen diffusion barrier that has the lowest free energy of oxide formation in the device. Various devices are disclosed as are varieties of carbon allotropes. Methods of protecting carbon, such as diamond from the oxygen etching in processes such as device manufacture are also disclosed.

23 Claims, 12 Drawing Sheets

INTEGRATION OF DISSIMILAR MATERIALS FOR ADVANCED MULTIFUNCTIONAL DEVICES

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

RELATED APPLICATIONS

This application claims the benefit under Title 35, United States Code §119(e) of U.S. provisional application Ser. No. 60/740,339 filed Nov. 29, 2005.

FIELD OF THE INVENTION

This invention relates to integrating dissimilar materials in a heterostructure to produce devices in the range from macro to nanoscale and particularly to the protection of carbon from reaction with oxygen during processing, whether or not an oxide is present in the final heterostructure.

BACKGROUND OF THE INVENTION

The materials integration processes described herein apply to a wide range of macro to nanodevices from macro, micro, and nanoresonators suitable for the fabrication of high frequency devices, to RF MEMS switches, to sensor structures suitable for producing high-sensitivity, high-selectivity, high-resolution, high-dynamic range bio-sensors based on high frequency resonators, to implantable biodevices for prostheses such as an artificial retina to restore sight to people blinded by retina degeneration. The micro and nanoresonators or RF MEMS switches are based on microelectromechanical system (MEMS) or nanoelectromechanical system (NEMS) structures. The resonator, RF switches or biosensor devices are based on horizontal or vertical cantilever-type or membrane-type structures. The biodevices involve Si-based microchips coated with hermetic carbon coatings or other biocompatible coatings that make the Si device biocompatible and resistant to corrosive bioenvironments such as the saline solution the human eye.

The inventive processes also produce microelectronic devices such as field effect transistors (FETs) that utilize the integration of both high dielectric constant layers with diamond layers (including single crystal, polycrystalline, or nano or ultrananocrystalline diamond).

Materials integration included in this invention are carbon thin films in any of their allotropic variants such as graphite, carbon nanotubes, and single crystal, microcrystalline, and nanocrystalline ultrananocrystalline diamond (UNCD), and diamond like carbon (DLC), complex oxide thin films including high dielectric constant, electro-optic, and ferroelectric thin films, and metallic films used as electrode materials.

This invention relates to a wide variety of devices produced with the inventive process, some of which are disclosed in copending patents, the entire disclosures of each are herein incorporated by reference. The devices which relate to or will benefit by the subject invention are disclosed in U.S. application Ser. Nos. 10/351,826, 11/073,263, 11/207,379, 11/388,636, 11/542,812, and U.S. Pat. No. 7,128,889 B2 issued Oct. 31, 2006 entitled "Method to Grow Carbon Thin Films Consisting Entirely of Diamond Grains 3-4 NM in Size and High-Energy Grain Boundaries.

SUMMARY OF THE INVENTION

Accordingly, it is a principal object of the present invention to provide a method or process and devices made thereby in which a variety of dissimilar materials including an oxygen containing material are combined with a carbon material or in which oxygen is present during formation.

Another object of the invention is to provide a device including a layered heterostructure with an oxygen-containing material, comprising a carbon layer, an amorphous oxygen diffusion barrier in contact with the carbon layer, and one or more of a metal, a carbide or an oxide in contact with the amorphous oxygen diffusion barrier, the amorphous oxygen diffusion barrier having the lowest free energy of oxide formation in the device.

Another object of the invention is to provide a piezoelectric driven device including a layered heterostructure with an oxygen-containing material, comprising a substrate, a carbon layer and a piezoelectric oxide layer, a pin hole-free amorphous oxygen diffusion barrier in contact with the carbon layer, and one or more of a metal, a carbide or an oxide in contact with the amorphous oxygen diffusion barrier, the amorphous oxygen diffusion barrier having the lowest free energy of oxide formation in the device.

A still further object of the invention is to provide a process for forming a layered heterostructure device including an oxygen-containing material, comprising providing a substrate, depositing a carbon layer on the substrate or on a layer on the substrate, depositing an amorphous oxygen diffusion barrier on the carbon layer, and providing one or more of a metal, a carbide or an oxide in contact with the diffusion layer, the amorphous oxygen diffusion barrier having the lowest free energy of oxide formation in the device.

A final object of the invention is to provide a process for protecting carbon from being etched by oxygen, comprising depositing an amorphous oxygen diffusion barrier on the carbon prior to exposing the carbon to oxygen, wherein the amorphous oxygen diffusion barrier has the lowest free energy of oxide formation of any material in contact with the carbon.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

Figure 1:
FIG. 1 is a cross-section TEM of BST/UNCD heterostructure layer without a TiAl oxygen diffusion barrier between the BST and the UNCD layers.

While the invention has been described principally with respect to carbon in the form of UNCD, it also includes, as previously stated, any allotrope of carbon including graphite, carbon nanotubes, single crystal, microcrystalline, nanocrystalline, ultrananocrystalline diamond and diamond-like carbon (DLC). The oxide thin films referenced in the invention include, but are not limited to high dielectric constant oxides, electro-optic oxides and ferro-electric oxide thin films. A wide variety of metallic films may be used as electrode materials or for that matter of fact, other materials depending on the device produced. Metals mentioned herein include Pt, W, Mo, and Ti as well as various alloys thereof, but for the carbide-forming layers, a wide variety of materials is available.

A wide variety of devices may be manufactured using the invention. For instance, both MEMS and NMS switches, capacitors, transistors, resonators, biosensors, and others all may be improved using the subject invention as a mechanism to protect carbon from the deleterious effects of oxygen.

DESCRIPTION OF THE PREFERRED EMBODIMENTS

Growth of high dielectric constant (K) thin films [e.g., $Ba_xSr_{1-x}TiO_3$ (BST)], ferroelectric/piezoelectric thin films [e.g., $PbZr_xTi_{1-x}O_3$ (PZT) family of materials or nitrides such as, but not limited to aluminum nitride, or electro-optic thin films [e.g., $KNbO_3$ (KNO)], or magnetic oxide films [e.g. La—Mn—Co—O (LMCO)], and any other complex oxide thin film on graphite, carbon nanotubes, single crystalline, microcrystalline, nanocrystalline, ultrananocrystalline diamond (UNCD) or DLC thin films or vice versa on appropriate platform materials such as semiconductor (e.g., silicon, silicon-germanium alloys, SiC), insulators (e.g., $SrTiO_3$), or metals (e.g., Pt, W, Mo, Ti) encounter the problem of etching the carbon layer in the presence of oxygen. With the present invention, carbon films can be grown on top of or in a heterostructure with complex oxide films to produce multilayers for fabrication of multifunctional devices.

Complex oxide thin films are generally grown at relatively high temperatures in an oxygen atmosphere and such conditions may result in degradation of carbon films due to chemical etching induced by oxygen reaction with carbon to form volatile CO and/or $CO_2$ species. Therefore, it is critical to develop diffusion barrier layers that enable the integration of complex oxide and carbon layers. The diffusion barrier layer should be preferably amorphous and impermeable to oxygen. TiAl alloys or Ti/Al multilayers provide such a barrier, via development of dense amorphous $TiAlO_x$ or TiAl with segregated $Al_2O_3$ layers. Although TiAl alloys and $Al_2O_3$ layers provide excellent diffusion barrier layers for the integration of oxide and carbon films, other alloys or elemental materials may also provide excellent barriers. The main characteristics of a diffusion barrier layer to protect carbon are: (1) the barrier layer needs to have an amorphous microstructure, and (2) the elements in the barrier need to have a free energy of oxide formation lower than that of the material they are protecting and preferably lower than any material in the device in order to bind oxygen preferentially. Any elemental or alloy material fulfilling these conditions works as a good diffusion barrier for oxygen, and then can be used for the integration of oxide and carbon layers proposed here.

Many devices require the integration of carbon films in any of the devices previously described with metallic layers that fulfill the role of electrodes. This integration is critical to the function of the device, and whether the integration requires that the carbon film is grown on top of the metallic film or vice versa, it is critical that the metallic and carbon layers form strong bonds and they are compatible from the point of view of chemical reactions and lattice and thermal mismatch. For example, the integration of UNCD films with metallic layers preferably requires a carbide interface layer between the metal and the UNCD. Therefore, tungsten (W), titanium (Ti), molybdenum (Mo) or any other metal that forms a carbide interface layer will provide a good metallic platform for integration of metal and UNCD layers for the fabrication of multifunctional devices.

The carbon films used in the multifunctional devices included in this invention can be produced by several methods such as microwave plasma chemical vapor deposition (MPCVD), filament assisted CVD, sputter deposition processes at ambient temperatures, or physical vapor deposition, such as but not limited to atomic layer deposition (ALD).

The complex oxide thin films used for the materials integration described in this invention can be produced by metalorganic chemical vapor deposition (MOCVD), metalorganic chemical (sol-gel) deposition, or physical vapor deposition. Complex oxide layers include, but are not limited to high dielectric constant (K) thin films [e.g., $Ba_xSr_{1-x}TiO_3$ (BST)], ferroelectric/piezoelectric thin films [e.g., $PbZr_xTi_{1-x}O_3$ (PZT) family of materials], or electro-optic thin films [e.g., $KNbO_3$ (KNO)], which can be and have been grown on graphite, carbon nanotubes, single crystalline, microcrystalline, nanocrystalline, or UNCD thin films, or vice versa, on appropriate platform materials such as a semiconductor (e.g., silicon, silicon-germanium alloys, SiC selenium, lead sulfide or other well known semiconductor materials), insulators (e.g., SrTiO$_3$), or metals (e.g., Pt, W, Mo, Ti). In addition, carbon films can be and have been grown on top of complex oxide films to produce multilayers for fabrication of multifunctional devices, see the incorporated applications and the '889 patent.

Because the growth of oxide layers requires relatively high temperatures (e.g. $\geqq 200°$ C.) in oxygen environments, it is necessary to deposit an oxygen diffusion barrier on top of the carbon film before growing the oxide layer or even a metal layer such as Pt to be used as an electrode layer, before growing the oxide layer on top. The diffusion barrier is necessary to avoid degradation of the carbon films due to chemical etching induced by oxygen reaction with carbon that form volatile CO and/or CO$_2$ species. The oxygen diffusion barrier layer can be deposited by metal-organic chemical vapor deposition (MOCVD), molecular beam epitaxy (MBE), atomic layer deposition (ALD), or physical vapor deposition such as sputter deposition at room or ambient temperature, or any other method suitable for growing oxide thin films. The diffusion barrier layer should preferably be amorphous and impermeable to oxygen and be pin-hole free. TiAl alloys or Ti/Al multilayers provide such a barrier via development of dense amorphous TiAlO$_x$ or TiAl with segregated Al$_2$O$_3$ layers. Alternatively Al$_2$O$_3$ layers also provide a good oxygen diffusion barrier layer, again provided it is pin-hole free.

The metallic layers used in the integration described here can be deposited by various methods such as sputter- and pulsed laser ablation-deposition, chemical vapor deposition, and electron beam deposition. Metals such as W, Ti, Mo, Pt, Cu among others may be used for the integration, where in the case of Pt or Cu that do not form appropriate carbides such as or Ti, layered structure such as W/Cu or Ti/Cu enables the integration of high conduction metals with carbon films via use of the carbide forming metal as an interface layer to provide the integration.

Referring now to FIG. 1, there is disclosed a TEM of a BST/UNCD heterostructure without amorphous oxygen diffusion barrier therebetween. The Figure shows the extreme etching of the diamond layer due to the presence of oxygen during the growth of the BST film.

Figure 2A:
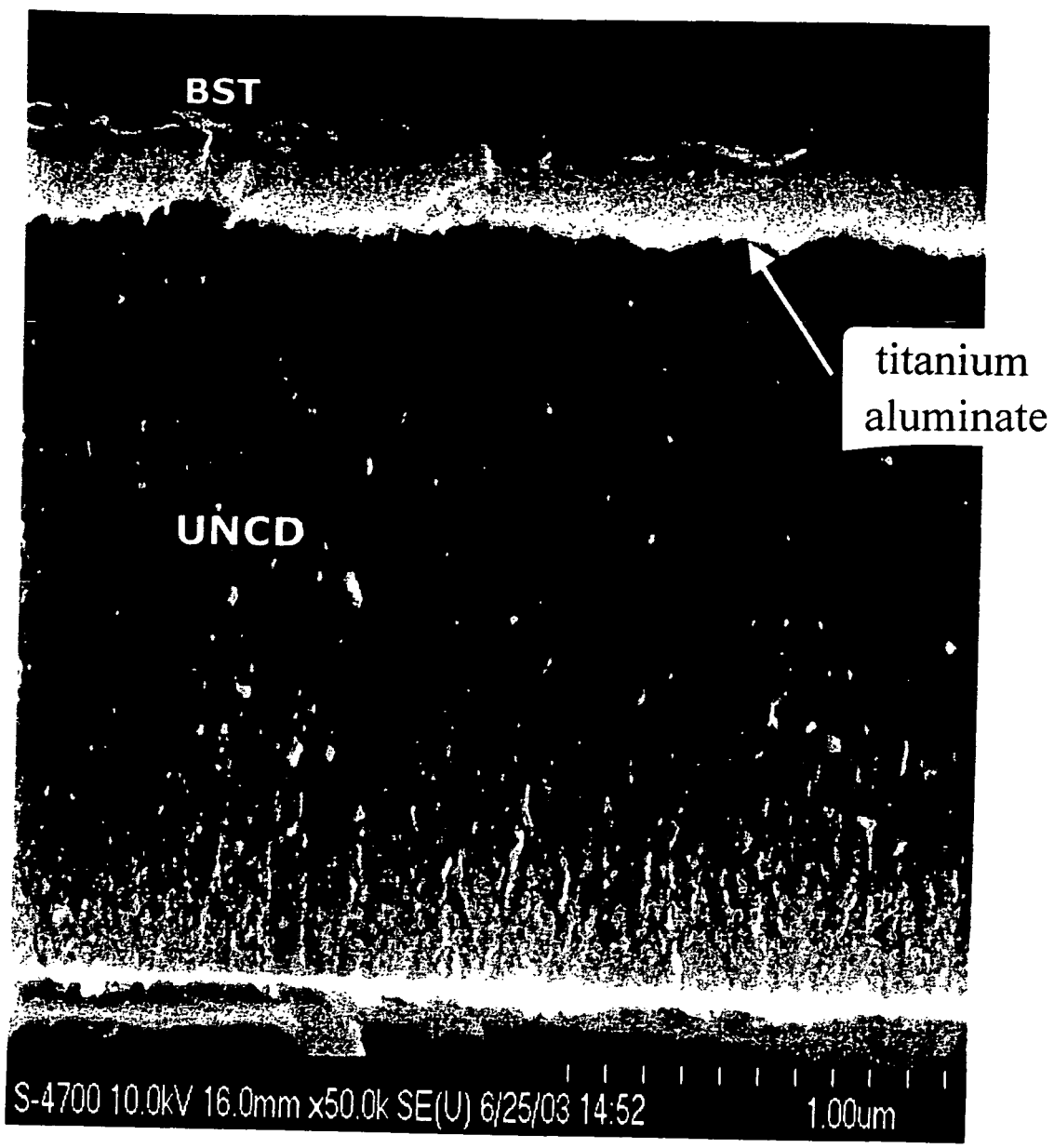
FIG. 2(a) is a cross-section TEM a BST/TiAl/UNCD heterostructure showing the excellent protection of the UNCD layer by the TiAl oxygen diffusion barrier during growth of BST films under the same conditions as in FIG. 1.
Figure 2B:
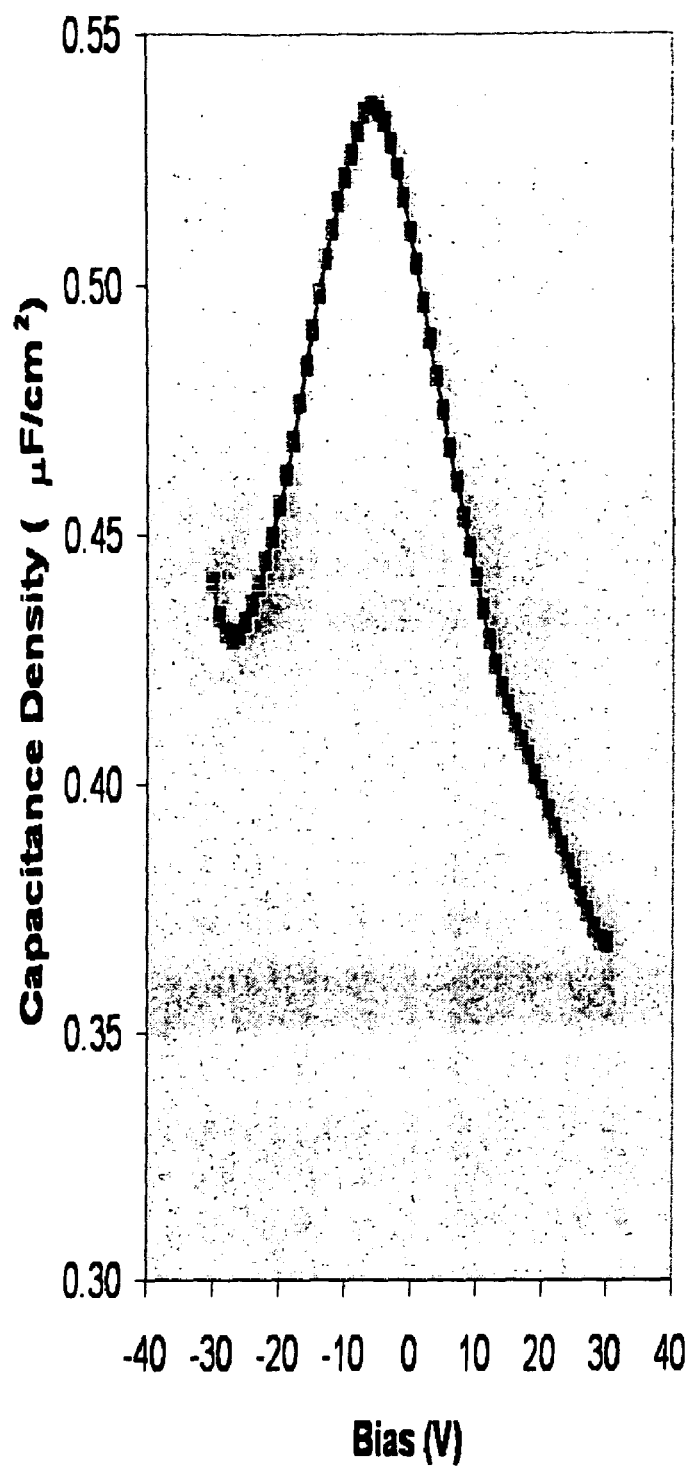
FIG. 2(b) is a cross-section TEM capacitance vs. voltage variation of a Pt/BST/TiAl/UNCD capacitor showing good tenability (capacitance variation with voltage) the BST capacitor.
Figure 2C:
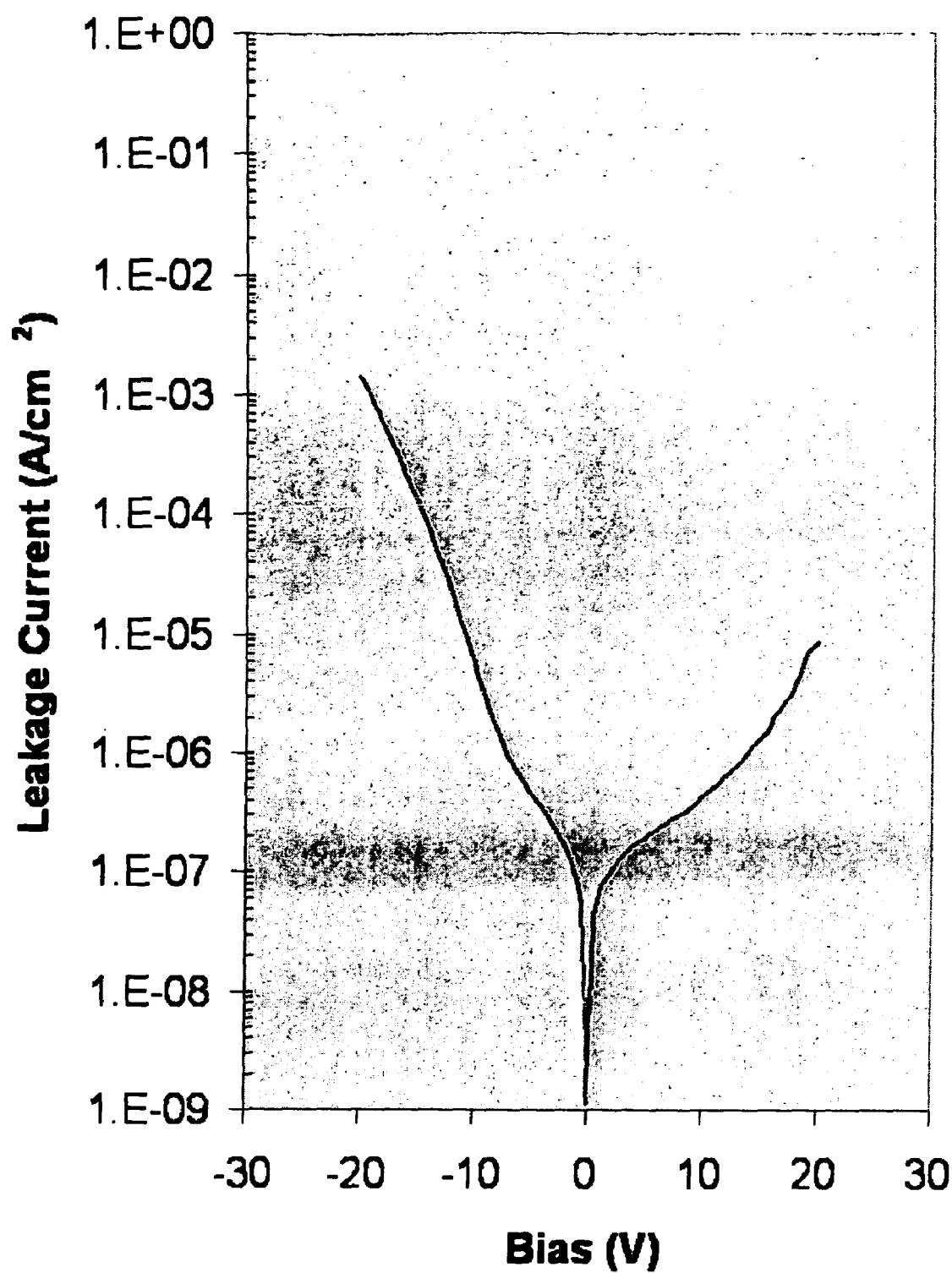
FIG. 2(c) is a cross-section TEM of the leakage current of the same capacitors as in (b) showing very low leakage as required for this type of capacitor. In addition, the BST/UNCD capacitor exhibits low loss (0.07).

FIG. 2(a) shows a much improved TEM cross-section of a combination of a BST film deposition on an amorphous titanium aluminide layer which is pin-hole free and UNCD functioning as a capacitor, the operation of which is illustrated in FIG. 2(b) which is a graphical representation of the relationship between capacitance density and bias in volts for the capacitor of FIG. 2(a). FIG. 2(c) shows the relationship between the leakage of current in A/cm$^2$ vs the voltage for the capacitor of FIG. 2(a).

Figure 3A:
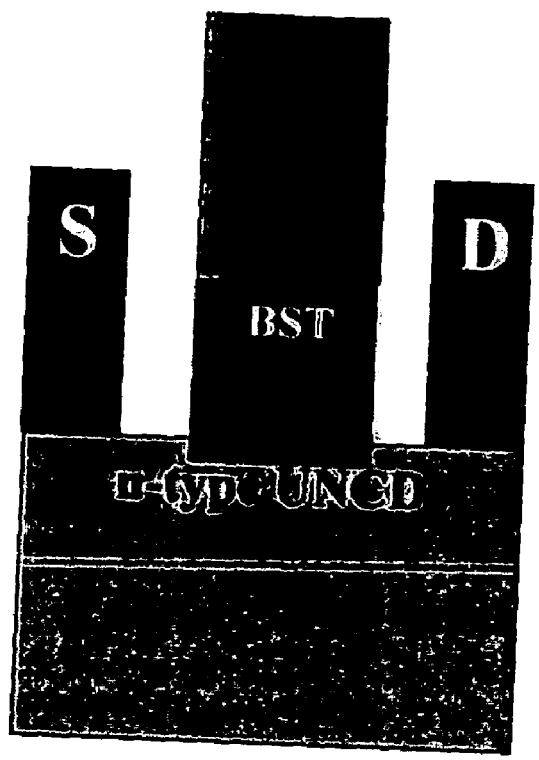
FIG. 3(a) is a schematic representation of MISFET involving a BST/UNCD integrated heterostructured layer.
Figure 3B:
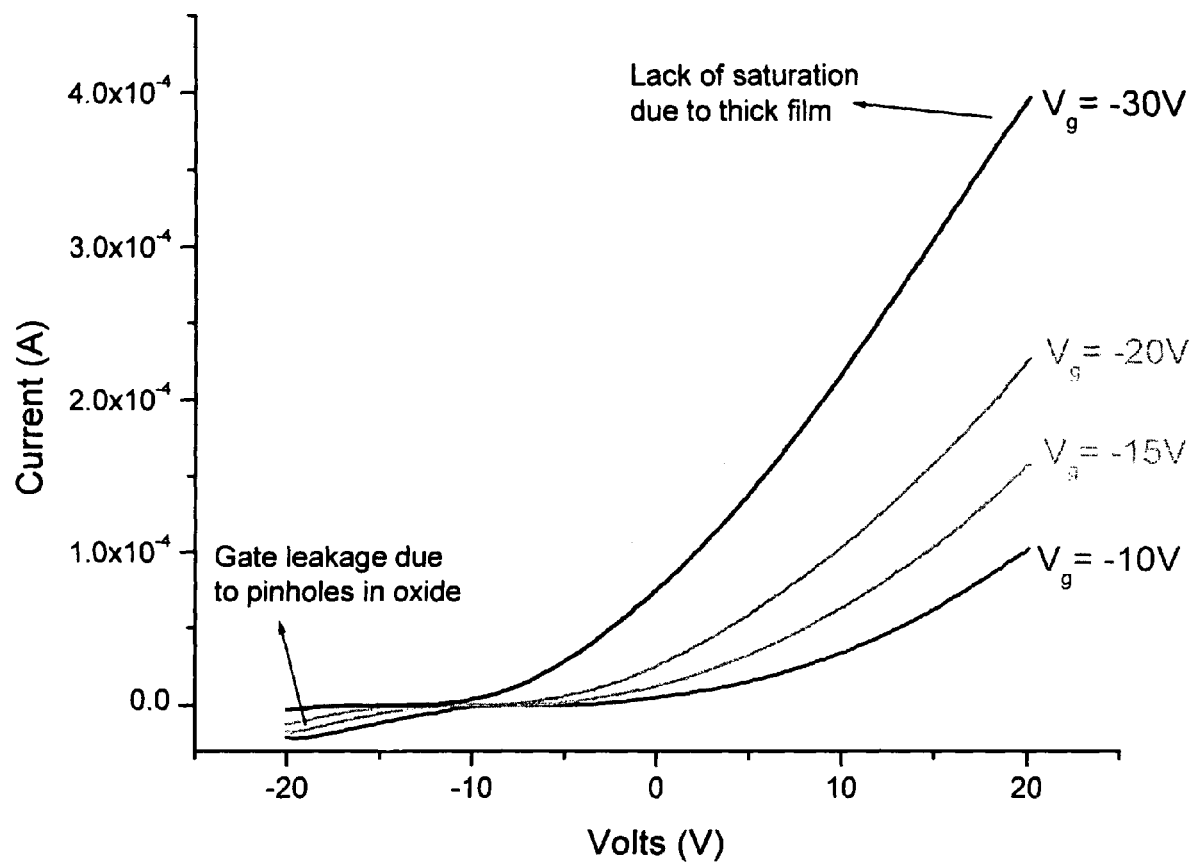
FIG. 3(b) is a graphical representation of the electrical characteristic of the MISFET shown in FIG. 3(a)

FIG. 3(a) is a schematic representation of a heterostructure metal-insulator-semi-conductor-field effect transition (MISFET) which includes a BST layer deposited on a silicon substrate. The UNCD layer is electrically conducting due to the presence of nitrogen at the boundaries at the UNCD crystals, these being 3-4 nm in average diameter. The MISFET of FIG. 3(a) may be used in corrosion resistance, high-performance electrodes for fuel cells, see FIG. 3(b) which is a graphical relationship of the current voltage for the MISFET of FIG. 3(a).

Figure 4:
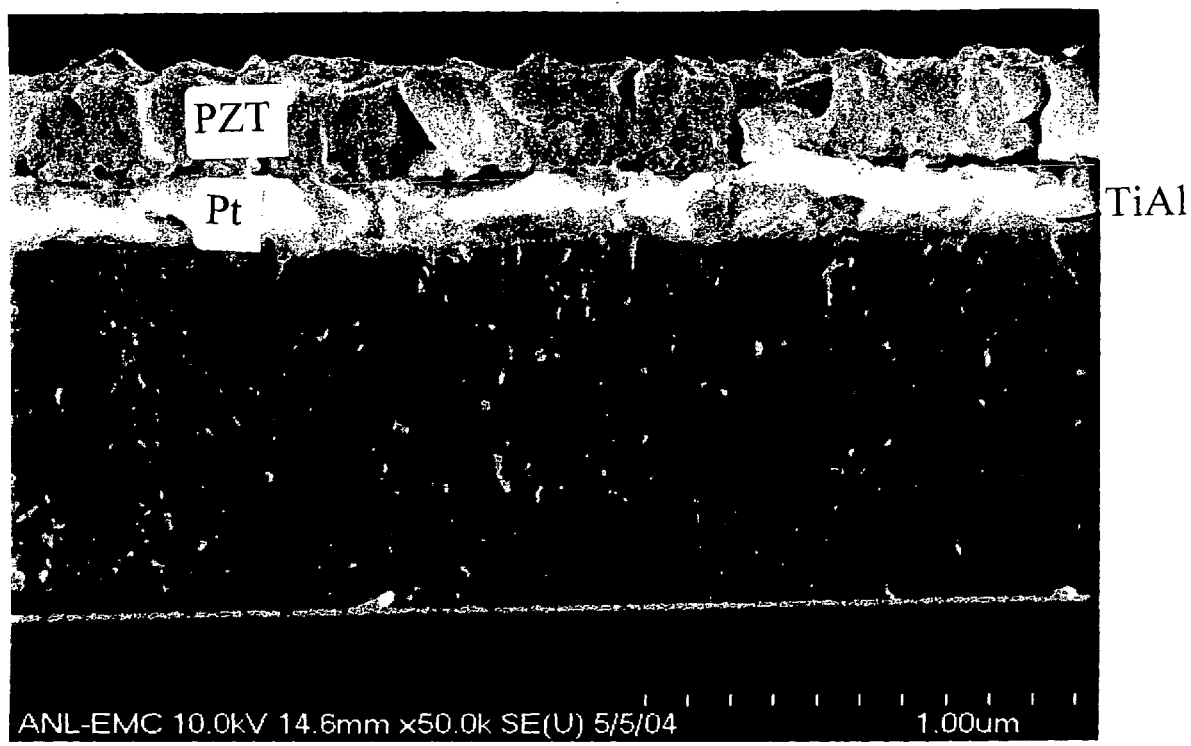
FIG. 4 is a cross-section TEM of $PbZr_xTi_{1-x}O_3$/Pt/TiAl/UNCD: TiAl layer enabling Piezo/diamond integration.

Reference to FIG. 4 shows a portion of a piezoelectric cantilever in which a thin film of PbZr$_x$Ti$_{1-x}$O$_3$/PZT was deposited over a platinum layer which in turn was deposited over a pin-hole free TiAl amorphous oxygen diffusion layer which had been deposited over a UNCD layer. As previously stated, the piezoelectric devices are useful in MEMS and NEMS either as cantilever type or membrane type structures.

Figure 5:
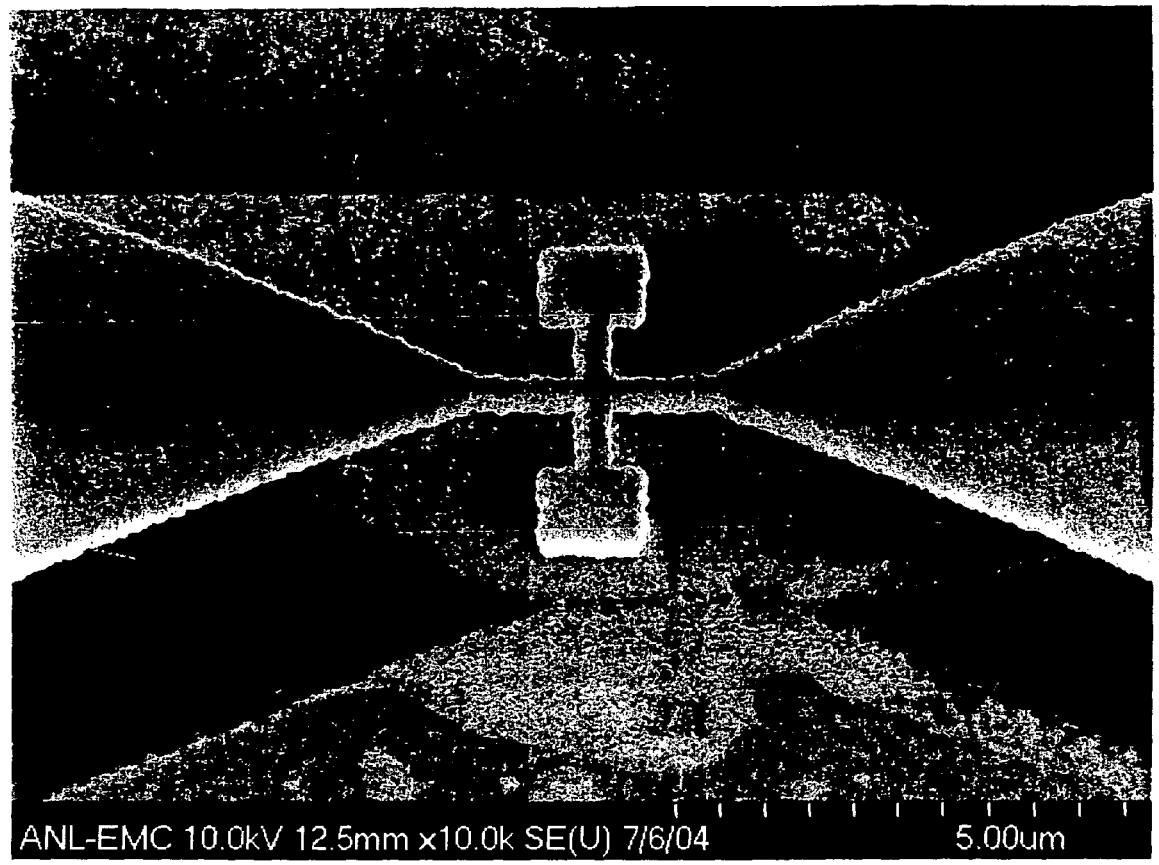
FIG. 5 is a cross-section TEM of a first PZT/UNCD hybrid nanoscale resonator.
Figure 6:
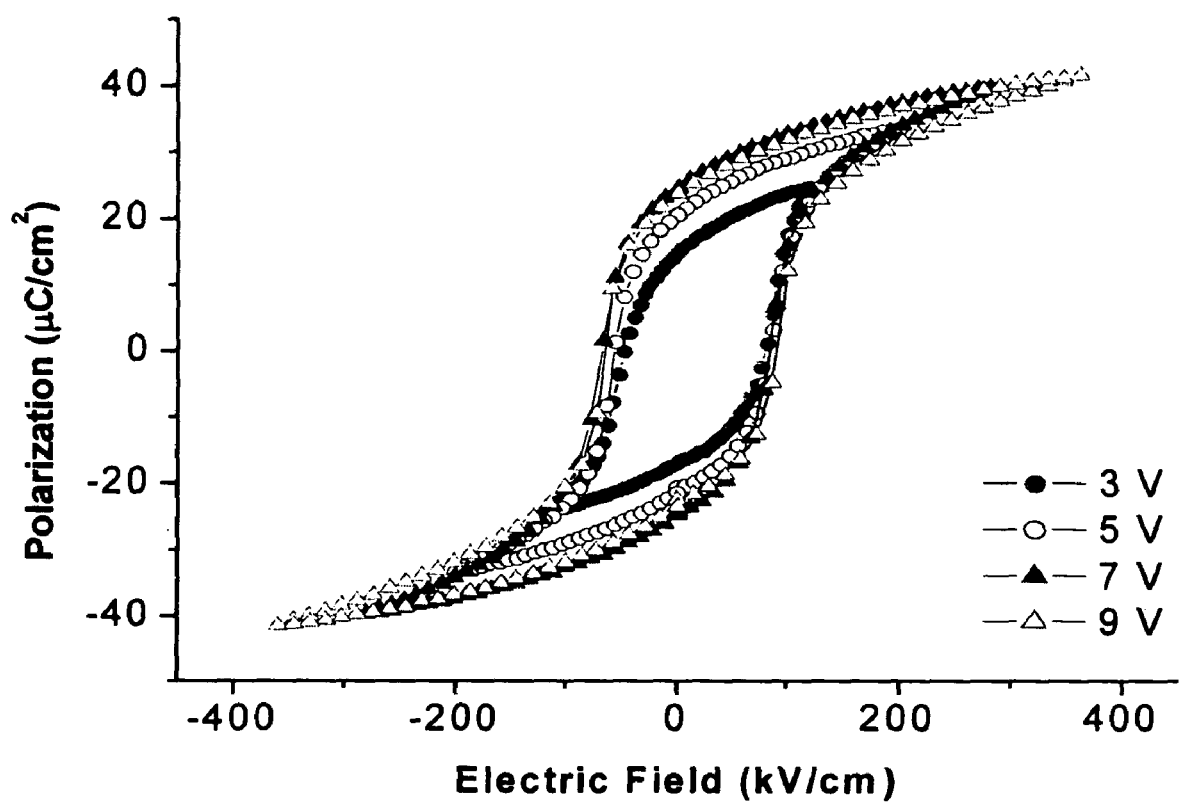
FIG. 6 is a graphical representation of the polarization and the electric field for a first Pt/PZT/Pt/TiAl/UNCD capacitor with excellent properties demonstrated.

FIG. 5 is a TEM of a PZT/UNCD hybrid nanoscale resonator and FIG. 6 is a graphical representation of the polarization against the electric field for a platinum/PZT/platinum/titanum aluminide/UNCD capacitor.

Figure 7:
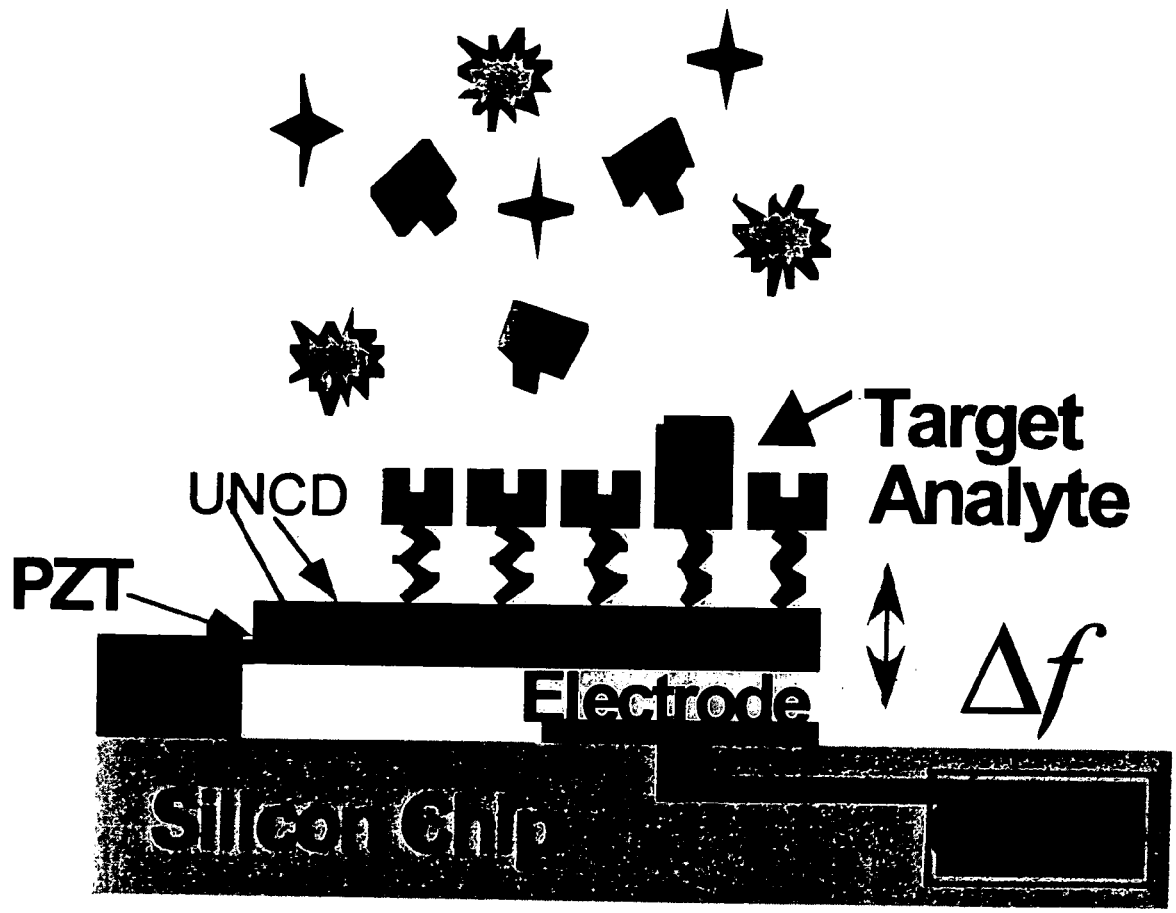
FIG. 7 is a schematic representation of PZT/UNCD integrated cantilever-based resonator using oxide/UNCD integration.

FIG. 7 is a schematic representation of a PZT/UNCD integrated cantilever based biosensor using an oxide and UNCD integrated according to the process of the present invention.

Figure 8A:
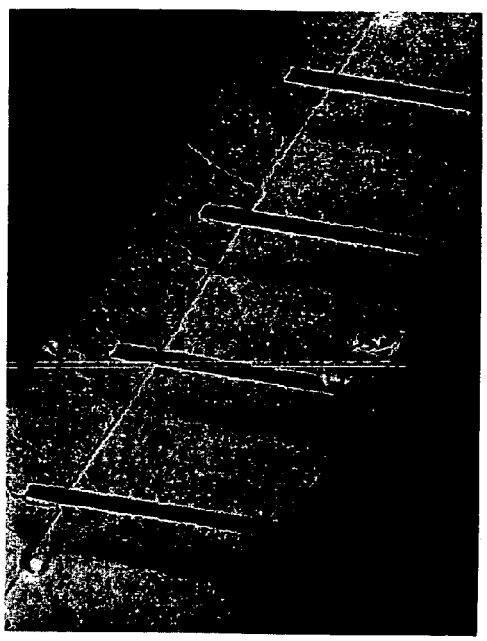
FIG. 8(a) is a cross-section TEM of UNCD cantilevers that can be integrated with $Pb(Zr_xTi_{1-x})O_3$ (PZT) piezoelectric layers to produce piezoactuated UNCD cantilevers for resonators, bio-compatible devices.
Figure 8B:
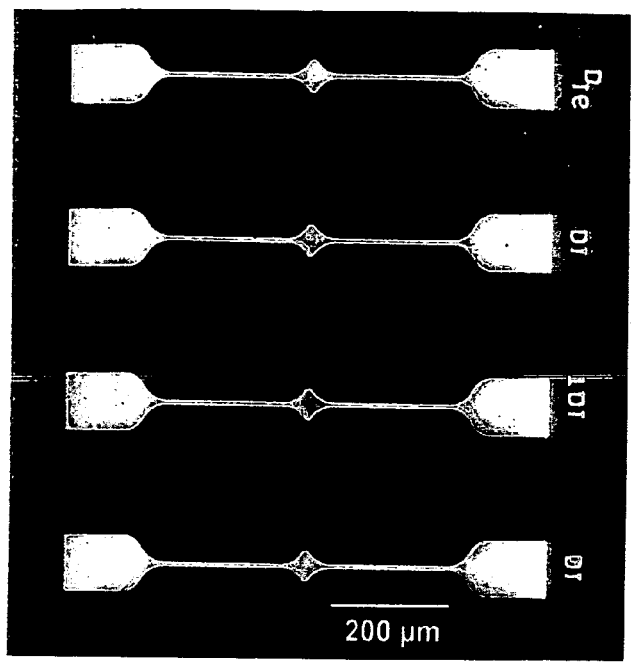
FIG. 8(b) is a cross-section TEM of UNCD membranes that can be integrated with $Pb(Zr_xTi_{1-x})O_3$ (PZT) piezoelectric layers to produce piezoactuated UNCD cantilevers for resonators, bio-compatible devices.

FIG. 8(a) is a UNCD cantilever and FIG. 8(b) is a UNCD membrane, each of which may be integrated with PZT piezoelectric layers to produce UNCD cantilevers for resonators, or bio-compatible devices.

Figure 9:
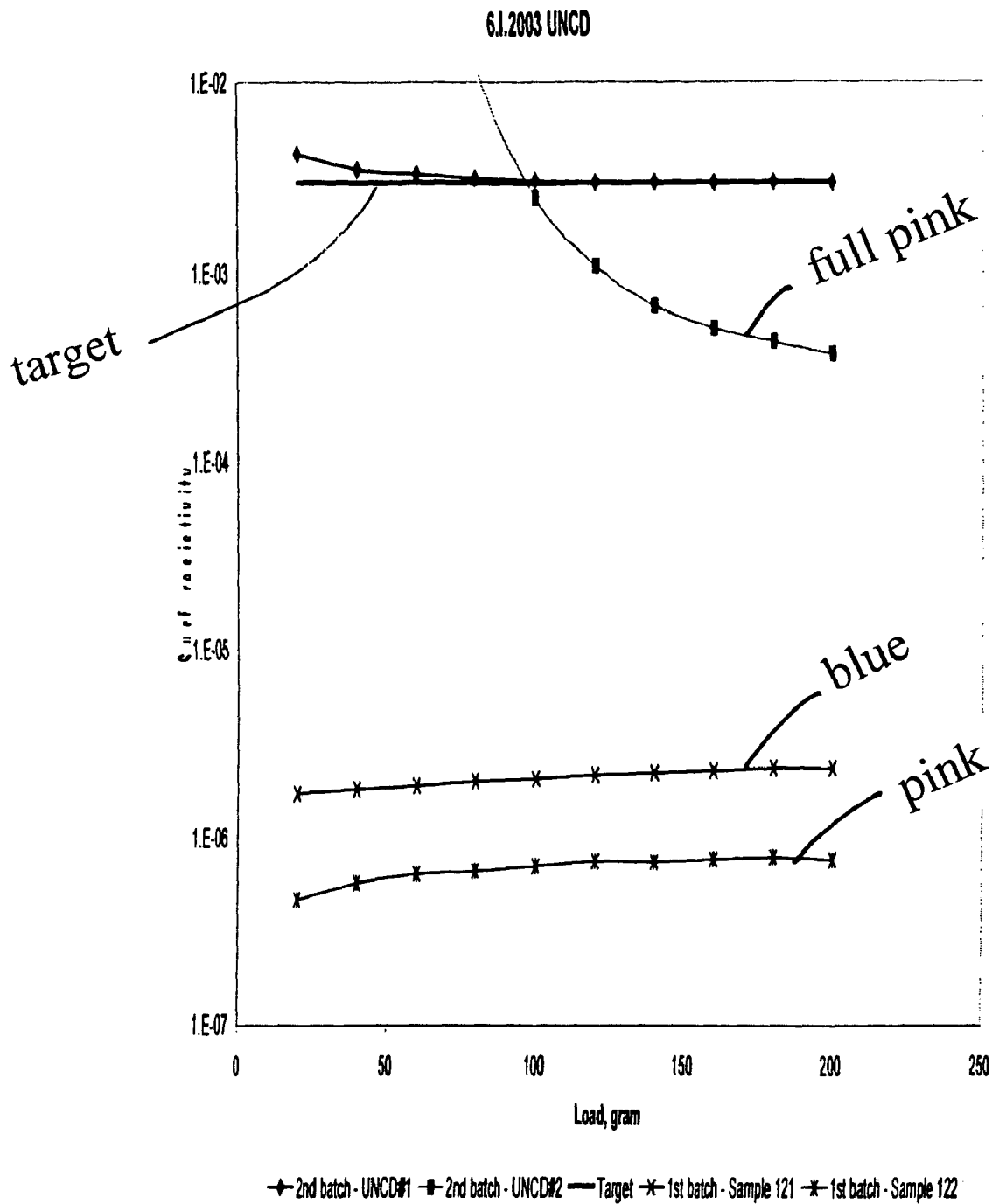
FIG. 9 is a graphical representation of the surface resistance vs. load grams for UNCD/Ti fuel cell electrodes. The curves for optimized UNCD samples 121 (blue x) and 122 (pink x) are about three orders of magnitude lower than the target resistance for fuel electrodes (full pink line), indicating that the UNCD/Ti electrode exhibits an excellent performance.

FIG. 9 is a graphical representation of the relationship between surface resistance and load grams for UNCD/Ti fuel cell electrodes. The curves for optimized UNCD samples therein, the blue "x" and pink "x" for samples 121 and 122 are about three orders of magnitude lower than the resistance for common fuel cell electrodes indicating that the UNCD/Ti electrode provides excellent performance.

The invention includes, as has been described, a layered heterostructure of a carbon layer and an amorphous oxygen diffusion barrier, preferably in contact therewith. Other layers in the heterostructure include one or more of a metal, a carbide, an oxide, a nitride or various other materials incorporated in MEMS or NEMS devices. The carbon may be any allotrope including various forms of diamond, diamond-like material, graphite or carbon nanotubes. When semiconductor material is present then a bonding layer of a carbide-forming material is introduced between the carbon layer and semiconductor layer, preferably a transition metal.

The amorphous oxygen diffusion layer is preferably dense and pin-hole free having the lowest free energy of oxide formation of any material in the device. Preferred materials are TiAl oxide, Ti and Al$_2$O$_3$, Al$_2$O$_3$ and tantalum aluminate. Piezoelectric driven devices are included in the invention incorporating the amorphous oxygen diffusion barrier and may either be cantilever or diaphragm devices. Preferably piezoelectric materials are PZT and aluminum nitride. Resonators, RF switches, transistors and biocompatible devices are included in the invention. The invention also includes methods of making the disclosed devices and a method of protecting a carbon material during patterning such as in a reaction ion etching (RIE) step during production of a device.

While the invention has been particularly shown and described with reference to a preferred embodiment hereof, it will be understood by those skilled in the art that several changes in form and detail may be made without departing from the spirit and scope of the invention.

The embodiments of the invention in which an exclusive property or privilege is claimed are defined as follows:

1. A device including a layered heterostructure with an oxygen-containing material, comprising
   a carbon layer,
   an amorphous Ti/Al alloy oxygen diffusion barrier in contact with said carbon layer, and
   one or more of a metal, a carbide or an oxide in contact with said amorphous oxygen diffusion barrier,
   said amorphous oxygen diffusion barrier having the lowest free energy of oxide formation in said device.

2. The device of claim 1, wherein said carbon layer is selected from the group consisting of diamond, diamond-like material, graphite, carbon nanotubes (CNTs) and mixtures thereof.

3. The device of claim 1, wherein said carbon layer includes microcrystalline diamond.

4. The device of claim 1, wherein said carbon layer includes nanocrystalline diamond.

5. The device of claim 1, wherein said carbon layer includes ultrananocrystalline diamond (UNCD).

6. The device of claim 1, wherein said carbon layer includes diamond-like material.

7. The device of claim 1, wherein said amorphous oxygen diffusion barrier includes aluminum oxide.

8. The device of claim 1, wherein said amorphous oxygen diffusion barrier includes titanium oxide.

9. The device of claim 1, wherein said amorphous oxygen diffusion barrier is pin hole free.

10. The device of claim 1, wherein a semiconductor material is present.

11. The device of claim 10, wherein said carbon layer is in contact with said semiconductor material.

12. The device of claim 10, wherein said carbon layer is in contact with an oxide of said semiconductor material.

13. The device of claim 10, wherein a carbide-forming layer is intermediate said carbon and said semiconductor material.

14. The device of claim 13, wherein said carbide-forming layer is a transition metal or mixtures or alloys thereof.

15. The device of claim 13, wherein said carbide-forming layer includes tungsten.

16. The device of claim 13, wherein said carbide-forming layer includes titanium.

17. The device of claim 13, wherein said carbide-forming layer includes molybdenum.

18. The device of claim 1, wherein said layers form at least in part a cantilever or membrane.

19. The device of claim 1, wherein said layers form at least in part a resonator.

20. The device of claim 1, wherein said layers form at least in part a radio frequency (RF) switch.

21. The device of claim 1, wherein at least one layer is biocompatible.

22. The device of claim 1, wherein said layers form at least in pan a transistor including a metallic portion and a high dielectric oxide portion.

23. The device of claim 1, wherein a piezoelectric material is present.

* * * * *

UNITED STATES PATENT AND TRADEMARK OFFICE
CERTIFICATE OF CORRECTION

| | | |
|---|---|---|
| PATENT NO. | : 7,791,201 B2 | Page 1 of 1 |
| APPLICATION NO. | : 11/607581 | |
| DATED | : September 7, 2010 | |
| INVENTOR(S) | : Orlando Auciello et al. | |

It is certified that error appears in the above-identified patent and that said Letters Patent is hereby corrected as shown below:

IN THE CLAIMS:

Column 8, Claim 22, line 16, delete the word "pan" and insert --part--.

Signed and Sealed this

Fourteenth Day of December, 2010

David J. Kappos
*Director of the United States Patent and Trademark Office*